US008362127B2

(12) United States Patent
Timberlake et al.

(10) Patent No.: US 8,362,127 B2
(45) Date of Patent: Jan. 29, 2013

(54) FLAME RETARDANT HALOGENATED PHENYL ETHERS

(75) Inventors: Larry D. Timberlake, West Lafayette, IN (US); James D. Siebecker, West Lafayette, IN (US); Subramaniam Narayan, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 78 days.

(21) Appl. No.: 13/248,387

(22) Filed: Sep. 29, 2011

(65) Prior Publication Data
US 2012/0065297 A1 Mar. 15, 2012

Related U.S. Application Data

(63) Continuation-in-part of application No. 12/692,887, filed on Jan. 25, 2010, now abandoned.

(51) Int. Cl.
C08K 5/06 (2006.01)
(52) U.S. Cl. ........ 524/371; 252/609; 524/370; 524/379; 524/380; 524/381; 524/384; 524/391; 524/464; 524/466; 524/469; 524/471; 524/473; 524/571; 524/575; 524/577; 524/578; 526/340; 526/342; 526/346; 526/347; 526/347.1; 658/639; 658/645; 658/647; 658/656; 658/661; 658/663; 570/182; 570/183; 570/252; 570/261
(58) Field of Classification Search ............... 252/609; 524/370, 371, 379, 380, 381, 384, 391, 464, 524/466, 469, 471, 473, 571, 575, 577, 578; 526/340, 342, 346, 347, 347.1; 568/639, 568/645, 647, 656, 661, 663; 570/182, 183, 570/252, 261
See application file for complete search history.

(56) References Cited

U.S. PATENT DOCUMENTS

| 3,228,910 | A |   | 1/1966  | Stamatoff et al. |         |
|-----------|---|---|---------|------------------|---------|
| 3,332,909 | A |   | 7/1967  | Farnham et al.   |         |
| 3,760,003 | A |   | 9/1973  | Asadorian et al. |         |
| 3,929,901 | A |   | 12/1975 | Darsow et al.    |         |
| 4,141,880 | A |   | 2/1979  | Nametz et al.    |         |
| 4,258,175 | A |   | 3/1981  | Chen             |         |
| 4,287,373 | A |   | 9/1981  | Garman et al.    |         |
| 4,341,890 | A |   | 7/1982  | Lindvay          |         |
| 4,870,153 | A |   | 9/1989  | Matzner et al.   |         |
| 5,112,897 | A | * | 5/1992  | Dever et al.     | 524/412 |
| 5,530,044 | A |   | 6/1996  | Mack et al.      |         |
| 6,756,470 | B2|   | 6/2004  | Keller et al.    |         |
| 6,891,014 | B2|   | 5/2005  | Keller et al.    |         |
| 8,158,038 | B2| * | 4/2012  | Timberlake et al.| 252/609 |
| 2002/0161174 | A1 |  | 10/2002 | Sasaki et al.  |         |
| 2007/0093582 | A1 | *| 4/2007  | Dawson et al.  | 524/411 |
| 2008/0269416 | A1 |  | 10/2008 | Timberlake et al. |      |
| 2010/0160516 | A1 | *| 6/2010  | Timberlake et al. | 524/371 |
| 2011/0028626 | A1 | *| 2/2011  | Timberlake et al. | 524/370 |
| 2011/0184107 | A1 | *| 7/2011  | Timberlake     | 524/371 |

FOREIGN PATENT DOCUMENTS

| EP | 0018632 A1  | 11/1980 |
|----|-------------|---------|
| EP | 1160267 A1  | 12/2001 |
| EP | 1288191 A   | 3/2003  |
| FR | 1301174     | 8/1962  |
| GB | 1182226     | 2/1970  |
| GB | 1265443     | 3/1972  |
| GB | 1415945     | 12/1975 |
| JP | 63281425    | 11/1988 |
| JP | 02129137    | 5/1990  |
| WO | 2008/134294 | 11/2008 |
| WO | 2008/156928 | 12/2008 |

OTHER PUBLICATIONS

Dhanesar et al—Synthesis and Stationary Phase Properties of Bromo Phenyl Ethers, Journal of Chromatography, 267 (1983), pp. 293-301.
Ley, S. V. and Thomas, A. W.—Modern Synthetic Methods for Copper-Mediated C(aryl)-O, C(aryl)-N, and C(aryl)-S Bond Formation; Angew. Chem. Int. Ed. 2003, 42, 5400-5449.
Sawyer, J. S.—Recent Advances in Diaryl ether Synthesis; Tetrahedron, 2000, 56, 5045-5065.
Lindley, James—Copper Assisted Nucleophilic Substitution of Aryl Halogen; Tetrahedron, 1984, 40(9), 1433-1456.
Frlan, R. And Kikelj, D.—Recent Progress in Diaryl Ether Synthesis; Synthesis, 2006, 14, 2271-2285.
Ungnade, H. E.—the Chemistry of the Diaryl Ethers; Chemical Reviews, 1946, 38, 405-414; citing Staudinger, H. and Staiger, F. Ann. 1935, 517, 67.
Hammann, W. C. and Schisla, R. M.—Synthesis of Seven New Polyphenyl Ethers; J. Chem. Eng. Data 1970, 15(2), 352-355.
Dort, et al, Poly-p-Phenylene Oxide; European Polymer Journal, 1968, 4, 275-287.
Jurek, M. J. and McGrath, J. E.—The Synthesis of Poly (Arylene ethers) via the Ullmann Condensation Reaction; Polymer Preprints 1987, 28(1), 180-1.
Dominguez, D. D. and Keller, T. M.—Low-melting Phthalonitrile Oligomers: Preparation, Polymerization and Polymer Properties; High Performance Polymers 2006, 18, 283-304.

(Continued)

Primary Examiner — Richard A Huhn
(74) Attorney, Agent, or Firm — Joseph Suhadolnik

(57) ABSTRACT

A halogenated non-polymeric phenyl ether flame retardant is described having the general formula (I):

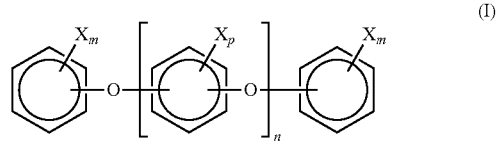

wherein each X is independently Cl or Br, n is an integer of 1 or 2, and each p is independently an integer of 1 to 4, provided that, when each X is Cl, the total amount halogen in the ether is from about 50 to about 65 wt % and when each X is Br, the total amount halogen in the ether is from at least 70 wt % to about 79 wt % and wherein from about 30% to about 80%, for example from about 35% to about 75% of the halogenated ethers are fully halogenated the remainder being partially halogenated. The present flame retardant provides superior mechanical properties when incorporated into a polymer than similar flame retardants which contain a higher amount of fully halogenated species.

19 Claims, No Drawings

OTHER PUBLICATIONS

Laskoski, M.; Dominguez, D. D. and Keller, T. M.—Oligomeric Cyanate Ester Resins: Application of a Modified Ullmann Synthesis in the Preparation of Thermosetting Polymers; J. Polym. Sci. A: Polym. Chem. 2006 44, 4559-4565.

Laskoski, M.; Dominguez, D. D. and Keller, T. M.—Synthesis and Properties of a Liquid Oligomeric Cyanate Ester Resin Polymer 2006, 47, 3727-3733.

Marcoux, J. F.; Doye, S. and Buchwald, S. L.—A General Copper-Catalyzed Synthesis of Diaryl Ethers; J. Am. Chem. Soc. 1997, 119, 10539.

Lindley, P. M.; Picklesimer, L. G.; Evans, B.; Arnold, F. E. and Kane, J. J. Arylether Sulfone Oligomers with Acetylene Termination from the Ullmann Ether Reaction, in ACS Symp. Ser. 282, Ch. 3, 1985, 31-42.

Hedberg, F. L.; Unroe, M. R.; Lindley, P. M. and Hunsaker, M. E.—A General Preparation of Tailored-length Acetylene Terminated Resins from Low Cost Bisphenols; Wright Patterson Air Force Base Technical Report AFWAL-TR-85-4041, 1985.

Lee, J. I.; Kwon, L. Y.; Kim, J.-H.; Choi, K.-Y. and Suh, D. H.—Synthesis of New Poly(aryl ether)s with Pendent Benzoxazole via Ullmann Ether Reaction; Die Angewandte Makromolekulare Chemie 1998, 254, 27-32, Lee, et al.

Chang, J. W. W. et al—Copper-catalyzed Ullmann Coupling Under ligand- and additive-free Conditions. Part 1: O-Arylation of phenols with aryl halides; Tet. Lett. 2008, 49, 2018-2022.

Williams, A. L.; Kinney, R. E. and Bridger, R. F.—Solvent-Assisted Ullmann Ether Synthesis. Reactions of Dihydric Phenols; J. Org. Chem. 1967, 32, 2501-2505.

Goodbrand, H. B. and Hu, N.-X.—Ligand-Accelerated Catalysts of the Ullmann Condensation: Application to Hole Conducting Triarylamines; J. Org. Chem. 1999, 64, 670-674.

Rao, H. et al—A Versatile and Efficient Ligand for Copper-Catalyzed Formation of C-N, C-O, and P-C Bonds: Pyrrolidine-2-Phosphonic Acid Phenyl Monoester; Chem. Eur. J. 2006, 12, 3636-3646; Wang, B.-A. et al Chinese J. Chem. 2006, 24, 1062-1065.

Ma, D. and Cai, Q.—N,N-Dimethyl Glycine-Promoted Ullmann Coupling Reaction of Phenols and Aryl Halides; Org. Lett. 2003, 5, 3799.

Cristau, H.-J. et al—A General and Mild Ullmann-Type Synthesis of Diaryl Athers; Org. Lett. 2004, 6(6), 913-916.

Ghosh, R. and Samuelson, A. G.—Copper Promoted Synthesis of Diaryl Ethers; New J. Chem. 2004, 28, 1390-1393.

Weingarten, H.J—Mechanism of the Ullmann Condensation; Org. Chem.1964, 29, 3624-3626.

Wang, B.-A. et al—Copper(II) and 2,2-Biimidazolyl-promoted Ullmann Coupling Reaction of Phenols and Aryl Iodides; Chinese J. Chem. 2006, 24, 1062-1065.

Timberlake et al.—Aryl Ether Oligomers and Process for Making Aryl Ether Oligomers—U.S. Appl. No. 12/533,558, filed Jul. 31, 2009.

De Pasquale et al. "Further Studies on Reactions of Perfluorophenolates with Substituted Pentafluorobenzenes and Perfluorocyclohexene" The Journal of Organic Chemistry. vol. 33, No. 2(1968) pp. 830-833.

Denivelle et al. " Sue l'oxydation de Phenols Benzeniques Pentahalogenes" C.R. Acad.Sc.Paris Serie C. vol. 272 (1971) pp. 653-656.

* cited by examiner

FLAME RETARDANT HALOGENATED PHENYL ETHERS

This application is a continuation in part of U.S. application Ser. No. 12/692,887, filed Jan. 25, 2010, the disclosure of which is incorporated herein in its entirety by reference.

FIELD

This invention relates to flame retardant halogenated phenyl ethers.

BACKGROUND

Decabromodiphenyl oxide (deca) and decabromodiphenylethane (deca-DPE) are commercially available materials widely used to flame retard various polymer resin systems. The structure of these materials is as follows:

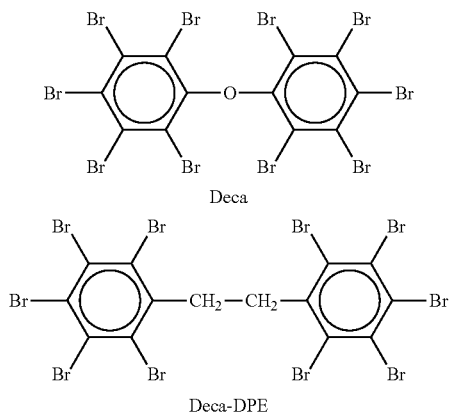

One of the advantages of using deca and deca-DPE in polymer resins that are difficult to flame retard, such as high-impact polystyrene (HIPS) and polyolefins, is that the materials have a very high (82-83%) bromine content. This allows a lower load level in the overall formulation, which in turn serves to minimize any negative effects of the flame retardant on the mechanical properties of the polymer.

Despite the commercial success of deca, there remains significant interest in developing alternative halogenated flame retardant materials that are equally or more efficient, not only because of economic pressures but also because they may allow lower flame retardant loadings, which in turn may impart improved performance properties. Improved properties, such as non-blooming formulations, or better mechanical properties can potentially be met by producing polymeric or oligomeric flame retardant compounds. These types of material tend to become entangled in the base resin polymer matrix, depending on the compatibility between the resin and the flame retardant, and hence should show fewer tendencies to bloom.

There are a number of commercially available flame retardant materials that can be considered oligomers or polymers of halogenated monomers. Examples of such halogenated monomers include tetrabromobisphenol A (TBBPA) and dibromostyrene (DBS), which have the following structures:

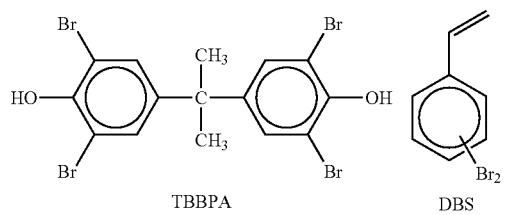

Commercially, TBBPA and DBS are typically not used in their monomeric form, but are converted into oligomeric or polymeric species. One class of oligomers is the brominated carbonate oligomers based on TBBPA. These are commercially available from Chemtura Corporation (examples include Great Lakes BC-52™, Great Lakes BC-52HP™, and Great Lakes BC-58™) and by Teijin Chemical (FireGuard 7500 and FireGuard 8500). These products are used primarily as flame retardants for polycarbonate and polyesters.

Brominated epoxy oligomers, based on condensation of TBBPA and epichlorohydrin, are commercially available and sold by Dainippon Ink and Chemicals under the Epiclon® series, and also by ICL Industrial Products (examples are F-2016 and F-2100) and other suppliers. The brominated epoxy oligomers find use as flame retardants for various thermoplastics both alone and in blends with other flame retardants.

Another class of brominated polymeric flame retardants based on TBBPA is exemplified by Teijin FG-3000, a copolymer of TBBPA and 1,2-dibromoethane. This aralkyl ether finds use in ABS and other styrenic polymers. Alternative end-groups, such as aryl or methoxy, on this polymer are also known as exemplified by materials described in U.S. Pat. Nos. 4,258,175 and 5,530,044. The non-reactive end-groups are claimed to improve the thermal stability of the flame retardant.

TBBPA is also converted into many other different types of epoxy resin copolymer oligomers by chain-extension reactions with other difunctional epoxy resin compounds, for example, by reaction with the diglycidylether of bisphenol A. Typical examples of these types of epoxy resin products are D.E.R.™ 539 by the Dow Chemical Company, or Epon™ 828 by Hexion Corporation. These products are used mainly in the manufacture of printed circuit boards.

DBS is made for captive use by Chemtura Corporation and is sold as several different polymeric species (Great Lakes PDBS-80™, Great Lakes PBS-64HW™, and Firemaster CP44-HF™) to make poly(bromostyrene) type flame retardants. These materials represent homopolymers or copolymers. Additionally, similar brominated polystyrene type flame retardants are commercially available from Albemarle Chemical Corporation (Saytex® HP-3010, Saytex® HP-7010, and PyroChek 68PB). All these polymeric products are used to flame retard thermoplastics such as polyamides and polyesters.

Unfortunately, one of the key drawbacks of the existing halogenated polymer materials is their relatively low halogen content, which makes them less efficient as flame retardants and consequently typically has a negative effect on the desirable physical properties of the flame retardant formulations containing them, such as impact strength. For example, whereas deca and deca-DPE contain 82-83% bromine, oligomers or polymers based on the brominated monomers mentioned above generally have a bromine content in the range of 52%-68%, depending on the material. This therefore typically requires a flame retardant loading level in a polymer formulation significantly higher than that required for deca, often resulting in inferior mechanical properties for the formulation.

In our U.S. Patent Application Publication No. 2008/0269416, we have proposed a new class of flame retardant materials that to not detract from the mechanical properties of the target resin and that are based on halogenated aryl ether oligomers comprising the following repeating monomeric units:

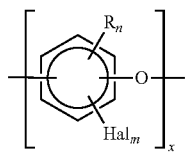

wherein R is hydrogen or alkyl, especially $C_1$ to $C_4$ alkyl, Hal is halogen, normally bromine, m is at least 1, n is 0 to 3 and x is at least 2, such as 3 to 100,000. These materials can be halogenated to a higher level than other currently available oligomeric flame retardants and provide superior mechanical properties when combined with resins such as HIPS and polyolefins as well as engineering thermoplastics such as polyamides and polyesters. It is also found that these aryl ether oligomers, even at lower levels of halogenation, give formulations with acceptable mechanical properties.

The materials disclosed in the '416 publication are polymeric in the sense that they have a molecular weight distribution resulting from the varying degrees of polymerization of the monomer units. In addition, it is known that certain discrete halogenated phenyl ether compounds, which have multiple phenyloxy linkages but which are not polymeric in the sense that they do not have a molecular weight distribution, have utility as flame retardants. For example, Japanese Unexamined Patent Application Publication 2-129,137 discloses flame retardant polymer compositions in which the polymer is compounded with a halogenated bis(4-phenoxyphenyl)ether shown by general formula [I]:

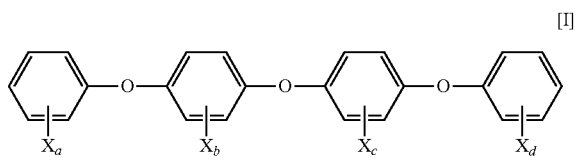

in which X is a halogen atom, a and d are numbers in the range of 1-5, and b and c are numbers in the range of 1-4. Materials containing from 64 to 81 wt % Br are exemplified in the application.

In addition, U.S. Pat. No. 3,760,003 discloses halogenated polyphenyl ethers having the general formula:

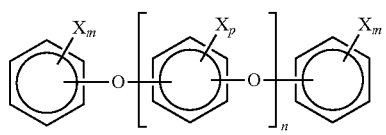

wherein each X is independently Cl or Br, each m is independently an integer of 0 to 5, each p is independently an integer of 0 to 4, n is an integer of 2 to 4, and 50% or more by weight of the compound is halogen. Perbrominated materials containing at least 60 wt % Br are said to be preferred.

Further the fully brominated polyphenyl ether (81.8 wt % Br), tetradecabromodiphenoxybenzene:

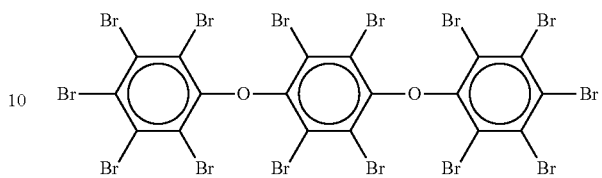

is sold by Albemarle Chemical Corporation under the trade name SAYTEX 120 for use as a flame retardant in high performance polyamide and linear polyester engineering resins and alloys, as well as in polyolefin and styrenic resins.

According to the present invention, it has now been found that certain non-polymeric phenyl ethers, when halogenated to a controlled level slightly below full halogenation, exhibit a unique combination of flame retardant efficiency and superior mechanical properties when combined with a wide variety of resin compositions. These exceptional properties are not due simply to the halogen content of the halogenated phenyl ether flame retardant, but also to the amount of fully halogenated compounds relative to the amount of partially halogenated compounds in a mixture of unequally halogenated phenyl ethers. Exceptional properties are found for mixtures that result from the controlled halogenation a single phenyl ether species as well as for mixtures of halogenated aryl ether oligomer compounds having different chain lengths, i.e., different numbers of linked phenoxy rings, provided that the correct proportion of fully halogenated to partially halogenated ethers is present.

SUMMARY

In one aspect, the invention resides in a halogenated non-polymeric phenyl ether flame retardant having the general formula (I):

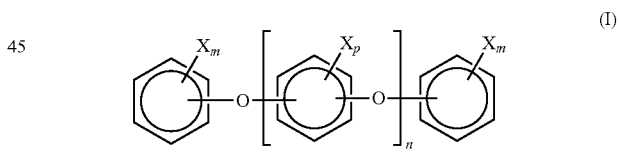

wherein each X is independently Cl or Br, n is an integer of 1 or 2, each m is independently an integer of 1 to 5 and each p is independently an integer of 1 to 4, provided that, when X is Cl, the total amount halogen in the ether is from about 50 to about 65 wt % and when, X is Br, the total amount halogen in the ether is from about 70 wt % to about 79 wt %, wherein the halogenated non-polymeric phenyl ether is a mixture of from about 30% to about 80%, for example from about 35% to about 75%, of fully halogenated phenyl ethers of formula I, i.e., each m is 5 and each p is 4, and from about 70% to about 20%, for example from about 65% to about 25% of partially halogenated phenyl ethers of formula I, i.e., at least one m is an integer of from 1 to 4 and/or at least one p is an integer from 1 to 3.

The halogenated phenyl ether flame retardant of the invention is not a single compound of formula I, rather the halogenated phenyl ether of the invention is a mixture of phenyl ether compounds wherein some are fully halogenated and some are partially halogenated.

The halogenated phenyl ether of the invention may contain one or more positional isomers of compounds of formula I. In one embodiment, at least one non-terminal phenyl group of formula I is connected to two phenoxy groups in the 1,4-positions. Alternatively, at least one non-terminal phenyl group can be connected to two phenoxy groups in the 1,3-positions or the 1,2-positions. In another embodiment, mixtures of positional isomers are present.

In another aspect of the invention, the halogenated phenyl ether flame retardant comprises a mixture of compounds of formula I wherein n is 1 with compounds of formula I wherein n is 2. Typically such a mixture also contains compounds of formula I wherein n is 0 and/or 3 or higher, provided that the percentage of all fully halogenated ethers of formula I is of from about 30% to about 80%, for example from about 35% to about 75%, and the percentage of all partially halogenated ethers of formula I is from about 70% to about 20%, for example from about 65% to about 25%, based on the total amount of all halogenated phenyl ethers of formula I.

In a further aspect, the invention resides in a flame retardant polymer composition comprising (a) a flammable macromolecular material, such as a thermoplastic or thermoset polymer, and (b) a flame retardant amount of a halogenated non-polymeric phenyl ether flame retardant having the general formula (I):

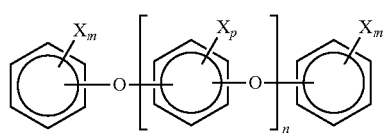

wherein each X is independently Cl or Br, n is an integer of 1 or 2, each m is independently an integer of 1 to 5 and each p is independently an integer of 1 to 4, provided that when X is Cl the total amount halogen in the ether is from about 50 to about 65 wt % and when X is Br the total amount halogen in the ether is from at about 70 wt % to about 79 wt %, wherein the halogenated non-polymeric phenyl ether is a mixture of from about 30% to about 80%, for example from about 35% to about 75%, of fully halogenated phenyl ethers of formula I, and from about 70% to about 20%, for example from about 45% to about 25% of partially halogenated phenyl ethers of formula I.

In another embodiment, the invention pertains to a polymer composition comprising, (a) flammable macromolecular material and (b) mixtures of halogenated non-polymeric phenyl ether of formula (I) wherein n is 1 and 2, and in another embodiment the polymer composition further comprises additional ethers of the general formula I wherein X, m and p are as previously defined but where n is 0 and/or 3 or higher. In each of these embodiments, the percentage of all fully halogenated ethers of formula I is of from about 30% to about 80%, for example from about 35% to about 75%, and the percentage of all partially halogenated ethers of formula I is from about 70% to about 20%, for example from about 65% to about 25%, based on the total amount of all halogenated phenyl ethers of formula I.

It has been found that polymer compositions containing halogenated ethers of general formula I of the instant invention with the identified amounts of fully halogenated and partially halogenated ethers have superior physical properties to similar compositions containing halogenated ethers of general formula I of the same halogen content but which contain a higher percentage of fully halogenated ethers. These physical properties are obtained while maintaining excellent flame retardance.

DETAILED DESCRIPTION

Described herein is a partially halogenated non-polymeric phenyl ether and its use as a flame retardant for flammable macromolecular polymers. Suitable macromolecular polymers include thermoplastic polymers, such as polystyrene, poly(acrylonitrile butadiene styrene), polycarbonates, polyolefins, polyesters and polyamides, and thermosetting polymers, such as epoxy resins, unsaturated polyesters, polyurethanes and rubbers.

The partially halogenated non-polymeric phenyl ether employed in the present blend or mixture has the general formula (I):

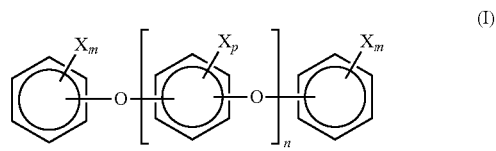

wherein each X is independently Cl or Br, n is an integer of 1 or 2, each m is independently an integer of 1 to 5 and each p is independently an integer of 1 to 4, provided that when X is Cl the total amount halogen in the ether is from about 50 to about 65 wt %, especially from about 60 wt % to about 64 wt %, and when X is Br the total amount halogen in the ether is from about 70 wt % to about 79 wt %, especially from about 71 wt % to about 78 wt %, such as about 71 wt % to about 76 wt %, wherein from about 30% to about 80%, for example from about 35% to about 75%, of the halogenated phenyl ethers of formula I are fully halogenated, and about 70% to about 20%, for example from about 65% to about 25% of the halogenated phenyl ethers of formula I are partially halogenated. In many embodiments, halogenated phenyl ethers of formula I wherein n is 1 and/or 2 are mixed or blended with phenyl ethers of formula I where n is 0 and/or 3 or higher.

In one embodiment, n is 1 and the partially halogenated non-polymeric phenyl ether has the formula (II):

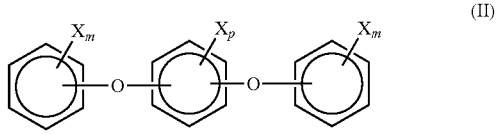

In another embodiment, n is 2 and the partially halogenated non-polymeric phenyl ether has the formula (III):

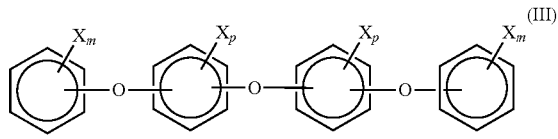

In each of the above embodiments, the phenoxy groups attached to the non-terminal phenyl groups may be totally or partially in the 1,4 (para)-position, the 1,3 (meta)-position or the 1,2 (ortho) position. For example, for a 3-ring phenyl ether of Formula (II), 3 configurations, para (3p), meta (3m) and ortho (3o), are possible for the phenoxy groups attached to the single non-terminal phenyl group:

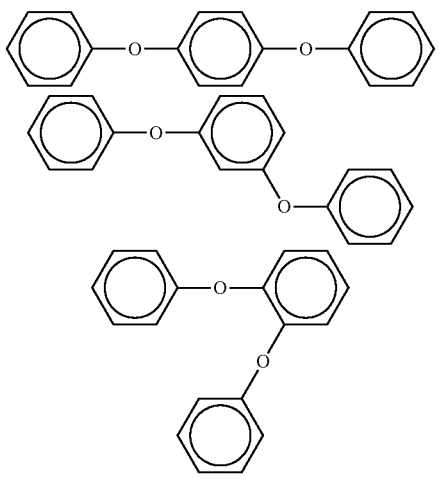

In the case of a 4-ring phenyl ether of formula (III), 6 configurations, 4 pp, 4 pm, 4 mm, 4po, 4mo and 4oo, are possible. Considering, for simplicity only the para and meta configurations, these are as follows:

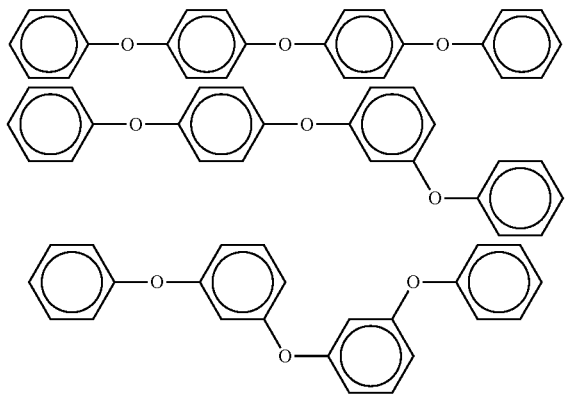

The level of bromination, i.e., X is Br, theoretically available for some of the 3-ring or 4-ring aryl ethers of formulas (II) and (III) is summarized as follows:

| Material | No. of Bromines Present | % OBr |
|---|---|---|
| 3-Ring | 7 | 68.7 |
| | 8 | 74.5 |
| | 9 | 74.0 |
| | 10 | 76.0 |
| | 11 | 77.8 |
| | 12 | 79.3 |
| | 13 | 80.7 |
| | 14 (max. possible) | 81.8 |
| 4-Ring | 9 | 67.6 |
| | 10 | 69.9 |
| | 11 | 71.9 |
| | 12 | 73.7 |

-continued

| Material | No. of Bromines Present | % OBr |
|---|---|---|
| | 13 | 75.3 |
| | 14 | 76.7 |
| | 15 | 77.9 |
| | 16 | 79.0 |
| | 17 | 80.1 |
| | 18 (max. possible) | 81.1 |

As seen from the above table, a brominated 4 ring phenyl ether flame retardant of formula I having a bromine content of 79.0% could be a single compound wherein 16 of the possible 18 rings are brominated, or it could be made up of any one of numerous combinations of fully brominated and non-fully brominated species. It has been found that, for example, a brominated 4 ring phenyl ether flame retardant of formula I with a bromine content of 79% provides better physical properties if certain specific combinations of fully brominated and partially brominated ethers are used, specifically those combinations wherein 30 to 80% of the brominated ethers are fully brominated (18 bromines present on the ether) and the remaining percent of brominated ethers containing fewer than 18 bromines.

For example, as detailed in the Experimental section, flame retardant high impact polystyrene compositions prepared with a flame retardant of the invention, i.e., 79% bromine content wherein 41% of the ethers of formula I are fully brominated, were compared with other otherwise identical compositions containing as flame retardant similar brominated ethers of formula I with 79% bromine content, but wherein 95% of the ethers of formula I are fully brominated. Each composition comprised 12.5% by weight of brominated ether flame retardant with similar amounts of 2, 3, 4, 5, 6, 7 and 8 ring phenyl ethers. Each composition exhibited excellent flame retardant properties. However, the compositions of the present invention, i.e., 41% fully brominated ethers, had significantly greater Gardner Impact strength, 64 in-lbs, and Notched Izod Impact strength, 2.89 ft-lb, than the comparative composition, i.e., 95% fully brominated ethers, Gardner Impact strength 7 in-lbs, Notched Izod Strength 1.91 in-lb.

The halogenated non-polymeric phenyl ether of the invention is produced by halogenation, normally bromination, of its associated phenyl ether precursor, which in turn can be made from the appropriate aryl halide and aryl hydroxyl compounds by the Ullmann aryl ether synthesis. Details of the Ullmann aryl ether synthesis can be found in the literature. Some review articles on this subject include Ley, S. V. and Thomas, A. W. *Angew. Chem. Int. Ed.* 2003, 42, 5400-5449; Sawyer, J. S. *Tetrahedron*, 2000, 56, 5045-5065; Lindley, James *Tetrahedron*, 1984, 40(9), 1433-1456; and Frlan, R. and Kikelj, D. *Synthesis*, 2006, 14, 2271-2285.

Bromination of the resultant phenyl ether precursor is readily achieved by the reaction of the phenyl ether with bromine in the presence of a Lewis acid catalyst, such as aluminum chloride. Depending on the amount of bromine desired to be introduced into the phenyl ether, the weight ratio of bromine to oligomer employed in the bromination reaction is typically between about 3.5:1 and about 9.0:1, such as between about 4.5:1 and about 7.0:1. The degree of bromination is typically controlled by the bromine stoichiometry of the reaction. Alternatively, in cases where excess bromine is used, the degree of bromination is controlled by either reaction time and/or by monitoring the amount of by-product HBr that is produced. In that case, the reaction could be stopped when the target bromination level is reached by adding a small amount of water to kill the catalyst.

Alternatively, bromine chloride may be used as the brominating agent to generate the desired product in similar fashion. In this case, a small amount of organically-bound chlorine would also be present, but would not detract from the properties of the final flame retardant.

It is often convenient or advantageous to use mixtures of halogenated phenyl ethers of differing chain lengths. Blends of halogenated phenyl ethers of the invention can be prepared by halogenating corresponding mixtures of non-halogenated phenyl ethers of various chain lengths, i.e., various number of phenoxy groups, or preparing halogenated phenyl ethers of a single chain length and blending with halogenated phenyl ethers of different chain lengths.

One embodiment provides a mixture or blend of halogenated ethers of formula I where n is 1, with halogenated ethers of formula I where n is 2. In other embodiments, ethers of the general formula I wherein n is 3 or higher are also present, provided that from about 30% to about 80%, for example from about 35% to about 75%, of all halogenated phenyl ethers are fully halogenated, and about 70% to about 20%, for example from about 65% to about 25% of all halogenated phenyl ethers are partially halogenated. A small amount of halogenated diphenyl ethers, usually less than 2%, may also be present. In the present invention however, the majority of halogenated phenyl ether components, i.e., 50% or more of all halogenated aryl ethers, are compounds of formula I wherein n is 1, compounds of formula I wherein n is 2, or a mixture of compounds of formula I wherein n is 1 with compounds of compounds of formula I wherein n is 2.

In one embodiment, the halogenated phenyl ether flame retardant comprises 50% or more of a combination of 3- and 4 ring halogenated phenyl ethers, i.e., compounds of formula I where n=1 and 2, and 50% or less of 2-, 5-, 6-, 7-, and/or 8 ring halogenated phenyl ethers, i.e., compounds of formula I where n=0, 3, 4, 5 and/or 6. Often, ethers with more than 8 phenyl rings are also present. Addition of this blend of ethers to a polymer resin via well known techniques provides a composition with excellent flame retardance and mechanical properties.

In another embodiment, the mixture of halogenated phenyl ethers comprises about 30 to about 50% 3-ring halogenated phenyl ethers, 30 to 60% 4-ring halogenated phenyl ethers, 1 to 15% 5-ring halogenated phenyl ethers and less than 15% total of halogenated phenyl ethers containing 2-, 6-, 7-, 8- or higher number of phenyl rings. Typically, the amount of halogenated diphenyl ethers is kept to a minimum, for example, from 0 to 2% and often from 0 to 1% or less of the total of halogenated phenyl ethers.

For example excellent results are obtained when blending into a polymer resin a halogenated phenyl ether flame retardant of the invention comprising:
from about 30 to about 45%, e.g., about 35 to about 45% of 3-ring halogenated phenyl ethers,
from about 35 to about 60%, e.g., about 35 to about 55% of 4-ring halogenated phenyl ethers,
from about 1 to about 10%, e.g., about 3 to about 10% of 5-ring halogenated phenyl ethers,
from about 1 to about 10%, e.g., about 3 to about 10% of 6-ring halogenated phenyl ethers,
from about 0.1 to about 4%, e.g., about 0.1 to about 3% of 7-ring halogenated phenyl ethers,
from about 0 to about 2%, e.g., about 0 to about 1.5% of 8-ring halogenated phenyl ethers, and
0 to about 1% of 2-ring halogenated di-phenyl ethers, wherein from about 30% to about 80%, for example from about 35% to about 75%, of all halogenated phenyl ethers are fully halogenated, and about 70% to about 20%, for example from about 65% to about 25% of all halogenated phenyl ethers are partially halogenated,
provided that when each X is Cl the total amount halogen in the ether is from about 50 to about 65 wt %, and when each X is Br the total amount halogen in the ether is from about 70 wt % to about 79 wt %.

The halogen, i.e., X in formula I, in most embodiments of the invention is bromine.

Because of its high thermal stability and its relatively high halogen content, the partially halogenated phenyl ether described herein can be used as a flame retardant for many different polymer resin systems. Surprisingly, the resultant flame retarded polymer systems are frequently found to exhibit the superior mechanical properties, such as impact strength, as compared with the same systems flame retarded with the fully halogenated ether counterpart.

Specific embodiments of this aspect of the invention include flame retardant polymer composition comprising
(a) a thermoplastic or thermoset polymer and
(b) a halogenated non-polymeric phenyl ether flame retardant having the general formula (I):

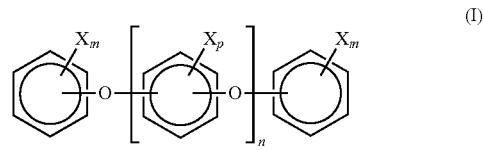

wherein each X is independently Cl or Br, n is an integer of 1 or 2, each m is independently an integer of 1 to 5 and each p is independently an integer of 1 to 4, provided that, when each X is Cl, the total amount halogen in the flame retardant is from about 50 wt % to about 65 wt % and when each X is Br, the total amount of halogen in the flame retardant is from about 70 wt % to about 79 wt %, and wherein about 30% to about 80% of the halogenated non-polymeric phenyl ethers of formula I present in the composition are fully halogenated, and about 70% to about 20% of all halogenated non-polymeric phenyl ethers are partially halogenated.

The preceding polymer composition, wherein about 35% to about 75% of all halogenated non-polymeric phenyl ethers are fully halogenated and about 65% to about 25% of all halogenated non-polymeric phenyl ethers are partially halogenated and/or wherein (b) comprises both halogenated non-polymeric phenyl ethers of general formula (I) wherein n is 1 and halogenated non-polymeric phenyl ethers of general formula (I) wherein n is 2.

The polymer composition wherein from about 5 to about 50% by weight of the total weight of the flame retardant polymer composition consists of halogenated phenyl ethers of general formula (I).

The polymer composition containing the flame retardant of the present invention wherein at least one non-terminal phenyl group in a compound of formula I is connected to two phenoxy groups in a 1,4-configuration, at least one non-terminal phenyl group in a compound of formula I is connected to two phenoxy groups in a 1,3-configuration and/or at least one non-terminal phenyl group in a compound of formula I is connected to two phenoxy groups in a 1,2-configuration.

Another embodiment is to a polymer composition comprising:

(a) a thermoplastic or thermoset polymer
(b) halogenated non-polymeric phenyl ethers of general formula (I) wherein n is 1 and halogenated non-polymeric phenyl ethers of general formula (I) wherein n is 2 and
(c) one or more halogenated non-polymeric phenyl ethers of general formula I wherein n is 3 or higher, each X is independently Cl or Br, each m is independently an integer of 1 to 5 and each p is independently an integer of 1 to 4, provided that,
when each X is Cl, the total amount of halogen in the halogenated non-polymeric phenyl ethers of (b) and (c) combined is from about 50 to about 65 wt %,
when each X is Br, the total amount of halogen in the halogenated non-polymeric phenyl ethers of (b) and (c) combined is from about 70 wt % to about 79 wt %, and
wherein about 30% to about 80%, for example, about 35% to about 75% of all halogenated non-polymeric phenyl ethers are fully halogenated, and about 70% to about 20%, for example about 65% to about 25%, of all halogenated non-polymeric phenyl ethers of (b) and (c) combined are partially halogenated.

Another embodiment pertains to the above composition comprising (a) the thermoplastic or thermoset polymer, (b) the mixture of 3- and 4-ring halogenated phenyl ethers of formula I, (c) 5-, 6-, 7-, and/or 8 ring halogenated phenyl ethers of formula I, and (d) optional di-phenyl ethers of formula I wherein n is 0, wherein the 3- and 4-ring halogenated phenyl ethers (b) comprise 50% or more of the combination of (b), (c) and (d).

For example, a polymer composition comprising (a), (b), (c) and (d) wherein the combination of (b), (c) and (d) comprises, based on the total weight of the combination,
about 30 to about 50% 3-ring halogenated phenyl ethers,
about 30 to about 60% 4-ring halogenated phenyl ethers,
about 1 to about 15% 5-ring halogenated phenyl ethers, and
less than 15% total of halogenated phenyl ethers containing 2-, 6-, 7-, 8- or a higher number of phenyl rings;

Such as a polymer composition as above wherein the combination of (b), (c) and (d) comprises,
from about 30 to about 45% of 3-ring halogenated phenyl ethers,
from about 35 to about 60% of 4-ring halogenated phenyl ethers,
from about 1 to about 10% of 5-ring halogenated phenyl ethers,
from about 1 to about 10% of 6-ring halogenated phenyl ethers,
from about 0.1 to about 4% of 7-ring halogenated phenyl ethers,
from about 0 to about 2% of 8-ring halogenated phenyl ethers, and
0 to about 1% of 2-ring halogenated di-phenyl ethers.

Typically, in the present polymer compositions, the halogen of the flame retardant, X in formula I, is bromine.

Generally, the halogenated phenyl ether is employed as a flame retardant with thermoplastic polymers, such as polystyrene, high-impact polystyrene (HIPS), poly(acrylonitrile butadiene styrene) (ABS), polycarbonates (PC), PC-ABS blends, polyolefins, polyesters and/or polyamides. With such polymers, the level of the partially halogenated phenyl ether in the polymer formulation required to give a V-0 classification when subjected to the flammability test protocol from Underwriters Laboratories is generally within the following ranges:

| Polymer | Useful | Preferred |
|---|---|---|
| Polystyrene | 5 to 25 wt % | 10 to 20 wt % |
| Polypropylene | 20 to 50 wt % | 25 to 40 wt % |
| Polyethylene | 5 to 35 wt % | 20 to 30 wt % |
| Polyamide | 5 to 25 wt % | 10 to 20 wt % |
| Polyester | 5 to 25 wt % | 10 to 20 wt %. |

The present halogenated phenyl ether can also be used with thermosetting polymers, such as epoxy resins, unsaturated polyesters, polyurethanes and/or rubbers. Where the base polymer is a thermosetting polymer, a suitable flammability-reducing amount of the halogenated phenyl ether is between about 5 wt % and about 35 wt %, such as between about 10 wt % and about 25 wt %.

Typical applications for polymer formulations containing the present halogenated phenyl ether as a flame retardant include automotive molded components, adhesives and sealants, fabric back coatings, electrical wire and cable jacketing, and electrical and electronic housings, components and connectors. In the area of building and construction, typical uses for the present flame retardant include self extinguishing polyfilms, wire jacketing for wire and cable, backcoating in carpeting and fabric including wall treatments, wood and other natural fiber-filled structural components, roofing materials including roofing membranes, roofing composite materials, and adhesives used to in construction of composite materials. In general consumer products, the present flame retardant can be used in formulation of appliance parts, housings and components for both attended and unattended appliances where flammability requirements demand.

The invention will now be more particularly described with reference to the following non-limiting Examples.

EXAMPLES

Example 1

Synthesis of Brominated 3p Phenyl Ether 1,4-diphenoxybenzene is prepared by the Ullmann ether synthesis as follows. 4-Phenoxyphenol (186.2 g, 1.0 mol) is dissolved in 1600 g of DMF with 300 mL toluene under nitrogen. A 50% KOH solution (112.0 g, 1.0 mol) is added followed by azeotropic removal of the water and stripping of the toluene. Bromobenzene (157.0 g, 1.0 mol) and cupric oxide (3.2 g, 0.04 mol) are then added and the reaction solution held at reflux (153° C.) for 24 hr. The DMF is then removed by stripping and the residue worked up to give 1,4-diphenoxybenzene.

Bromine (640.6 g) is added to a solution of 107.8 g of 1,4-diphenoxybenzene in 500 mL of dichloromethane containing 9.6 g of $AlCl_3$ catalyst. The reaction temperature is kept at 30° C. and the HBr off-gas is captured in a water trap. After the HBr evolution subsides, the material is worked up to give the product as an off-white solid. The material is analyzed to contain 72.6% bromine.

Example 2

Synthesis of Brominated 3p Phenyl Ether

The process of example 1 was repeated but with bromination being conducted by adding 334.8 g of bromine to a solution containing 50 g of 1,4-diphenoxybenzene with 5 g of AlCl₃ in 333 mL of chloroform. The material is analyzed to contain 74.2% bromine.

Example 3

Synthesis of Brominated 3m Phenyl Ether

The process of Example 1 is repeated but with the 4-phenoxyphenol being replaced by 3-phenoxyphenol.

Examples 4 to 13

Synthesis of Various Brominated Phenyl Ether Compounds

A similar procedure to that described in Example 1 is employed using the appropriate starting material substrate to generate the desired brominated aryl ether compounds, as shown in Table 1. The amount of bromine used was adjusted as needed.

Example 14

Compounding of Brominated Phenyl Ethers in HIPS Resin

The brominated phenyl ethers prepared in Examples 1 to 13 were compounded separately with HIPS (high impact polystyrene) resin formulations containing antimony oxide (ATO) synergist using a twin-screw extruder with barrel temperatures of 200 to 220° C. For comparison, a similar formulation was prepared using decabromodiphenyl oxide ("deca") as the flame retardant. The resultant formulations were injection-molded into 63.5 mm×12.7 mm×3 mm test bars and evaluated as shown in Table 1. The hod Notched Impact Strength (N-Impact in Table 1) values were measured according to ASTM D-256.

TABLE 1

| | | | HIPS Results | | | |
|---|---|---|---|---|---|---|
| Brominated Aryl Ether | | | N-Impact | Vicat, °C. | MFI, g/10 min (200° | |
| Example | Structure | % Br | ft-lb/in | (10N) | C., 5 Kg) | UL-94 |
| Deca | 2 | 83 | 2.1 | 96.3 | 11.6 | V-0 |
| 1 | 3 p | 72.6 | 2.8 | 94.0 | 19.6 | V-0 |
| 2 | 3 p | 74.2 | 3.0 | — | — | V-0 |
| 3 | 3 m | 72.4 | 3.3 | — | — | V-0 |
| 4 | 3 p | 79.6 | 1.9 | 97.4 | 8.5 | V-0 |
| 5 | 4 pp | 70.8 | 2.3 | 97.0 | 17.3 | V-0 |
| 6 | 4 mp | 74.7 | 2.9 | — | — | V-0 |
| 7 | 4 mp | 70.7 | 3.0 | — | — | V-0 |
| 8 | 4 pp | 75.1 | 2.8 | — | — | V-0 |
| 9 | 4 pp | 79.5 | 1.35 | 97.5 | 8.8 | V-0 |
| 10 | 5 ppp | 75.3 | 0.8 | 98.2 | 8.2 | V-0 |
| 11 | 5 ppp | 78.8 | 1.30 | 95.9 | 9.9 | V-0 |
| 12 | 5 pmp | 75.3 | 1.2 | — | — | V-0 |
| 13 | 5 mmm | 73.1 | 2.6 | — | — | V-0 |

As shown in Table 1, in both cases for 3 and 4-ring aryl ethers, the impact strength properties were inferior for the pure materials at the higher bromine levels. However, if slightly underbrominated, the impact strength improved. There is also an observed increase in the melt flow properties. Based on this data, the average number of bromines substituted on the 3-ring aryl ether should be less than around 12 per molecule (~79.3%) to achieve satisfactory impact strength properties. Likewise, the average number of bromines substituted on the 4-ring aryl ether should be less than around 16 per molecule (~79.0%) to achieve satisfactory impact strength.

The same improvement in impact strength is not observed with the partially and more fully brominated 5-ring aryl ethers tested. The influence of meta vs para substitution in this case seems to be a more dominant effect.

Example 15

Improved Physical Properties of HIPS Resin Compositions Comprising Brominated Phenyl Ethers Brominated phenyl ethers were prepared by brominating mixtures of phenyl ethers of general formula I, which mixtures comprised ethers wherein n was 0 through 6, wherein at least 50% of the ethers were compounds wherein n was 1 or 2, using procedures analogous to those above. Brominated ethers of formula I wherein n was explicitly 1, 2, 3, 4, 5, and 6 were also prepared following the above procedures. The products of the reactions yielded or were adjusted to provide mixtures of brominated ether compositions. Two compositions differing in the amount of fully brominated species were prepared having a bromine content of about 79% comprising the following oligomeric mixture:
approximately 40% of 3-ring brominated phenyl ethers,
approximately 47% of 4-ring brominated phenyl ethers,
approximately 5% of 5-ring brominated phenyl ethers,
approximately 5% of 6-ring brominated phenyl ethers,
approximately 2% of 7-ring brominated phenyl ethers,
approximately 1%% of 8-ring brominated phenyl ethers, and
less than 0.2% of 2-ring brominated di-phenyl ethers.

In brominated ether flame retardant Composition 15A, 41% of the brominated ethers were fully brominated. In brominated ether flame retardant Composition 15B, 95% of the brominated ethers were fully brominated.

Composition 15A and Composition 15B were compounded separately with HIPS (high impact polystyrene) resin formulations containing antimony oxide (ATO) synergist using a twin-screw extruder with barrel temperatures of 200 to 220° C. For comparison, a similar formulation was prepared using decabromodiphenyl oxide ("deca") as the flame retardant. Test samples using the resultant formulations were evaluated according to ASTM D-256 (Izod Notched Impact Strength) and ASTM D 5420-04 (Gardner Impact Strength, Dart Impact tester.) The data is shown in Table 2.

TABLE 2

| FR | Comp 15A | Comp 15B | Deca |
|---|---|---|---|
| % Br | 79.2 | 79.1 | 83 |
| HPLC A % Assay | 40.7 | 94.8 | — |
| Formulation | | | |
| % FR | 12.5 | 12.5 | 14 |
| % ATO TMS | 3.5 | 3.5 | 3.5 |
| % Kraton D1101 | 5 | 5 | 5 |
| % Anox PP18 | 0.2 | 0.2 | 0.2 |
| % HIPS | 78.8 | 78.8 | 77.3 |
| Final Properties | | | |
| UL-94 rating | V-0 | V-0 | V-0 |
| Notched Izod Impact, ft-lb/in | 2.89 | 1.91 | 2.36 |
| MFI, g/10 min. | 13.4 | 10.7 | 12.6 |
| Gardner Impact (in-lbs) | 64 | 7 | 15 |

As seen in Table 2, each HIPS sample exhibited excellent flame retardance, but the composition of the invention, Comp 15 A demonstrated superior physical properties.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What we claim is:

1. A flame retardant polymer composition comprising:
   (a) a thermoplastic or thermoset polymer and
   (b) a halogenated non-polymeric phenyl ether flame retardant comprising halogenated non-polymeric phenyl ethers of general formula (I):

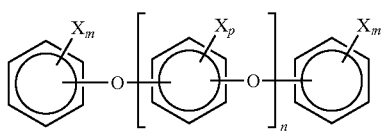

(I)

wherein each X is independently Cl or Br, n is an integer of 0, 1, 2, 3, 4, 5, or 6 or more, each m is independently an integer of 1 to 5 and each p is independently an integer of 1 to 4, wherein the flame retardant comprises, based on the total weight of halogenated non-polymeric phenyl ethers of formula (I):
   from about 30 to about 50% 3-ring halogenated phenyl ethers,
   from about 30 to about 60% 4-ring halogenated phenyl ethers,
   from about 1 to about 15% 5-ring halogenated phenyl ethers, and
   less than 15% total of halogenated phenyl ethers containing 2-, 6-, 7-, 8- or a higher number of phenyl rings,
provided that, when each X is Cl, the total amount halogen in the flame retardant is from about 50 wt % to about 65 wt % and when each X is Br, the total amount of halogen in the flame retardant is from about 70 wt % to about 79 wt %, and wherein from about 30% to about 80% of the halogenated non-polymeric phenyl ethers of formula (I) present in the composition are fully halogenated, and from about 70% to about 20% of all halogenated non-polymeric phenyl ethers are partially halogenated.

2. The composition of claim 1, wherein from about 35% to about 75% of all halogenated non-polymeric phenyl ethers are fully halogenated and from about 65% to about 25% of all halogenated non-polymeric phenyl ethers are partially halogenated.

3. The polymer composition of claim 1, wherein from about 5 to about 50% by weight of the total weight of the polymer composition consists of halogenated phenyl ethers of general formula (I).

4. The composition of claim 1, wherein each X is bromine.

5. The composition of claim 1, wherein at least one non-terminal phenyl group in a compound of formula (I) is connected to two phenoxy groups in a 1,4-configuration, at least one non-terminal phenyl group in a compound of formula (I) is connected to two phenoxy groups in a 1,3-configuration, and/or at least one non-terminal phenyl group in a compound of formula (I) is connected to two phenoxy groups in a 1,2-configuation.

6. The composition of claim 4, wherein from about 35% to about 75% of all halogenated non-polymeric phenyl ethers are fully halogenated and from about 65% to about 25% of all halogenated non-polymeric phenyl ethers are partially halogenated.

7. The polymer composition of claim 4, wherein from about 5 to about 50% by weight of the total weight of the polymer composition consists of the halogenated phenyl ethers.

8. The composition of claim 1, wherein the flame retardant comprises, based on the total weight of the halogenated non-polymeric phenyl ethers of formula (I),
   from about 30 to about 45% of 3-ring halogenated phenyl ethers,
   from about 35 to about 60% of 4-ring halogenated phenyl ethers,
   from about 1 to about 10% of 5-ring halogenated phenyl ethers,
   from about 1 to about 10% of 6-ring halogenated phenyl ethers,
   from about 0.1 to about 4% of 7-ring halogenated phenyl ethers,
   from about 0 to about 2% of 8-ring halogenated phenyl ethers, and
   0 to about 1% of 2-ring halogenated di-phenyl ethers.

9. The composition of claim 8, wherein each X is bromine.

10. The composition of claim 8, wherein at least one non-terminal phenyl group in a compound of formula (I) is connected to two phenoxy groups in a 1,4-configuration, at least one non-terminal phenyl group in a compound of formula (I) is connected to two phenoxy groups in a 1,3-configuration, and/or at least one non-terminal phenyl group in a compound of formula (I) is connected to two phenoxy groups in a 1,2-configuation.

11. The polymer composition of claim 9, wherein the thermoplastic or thermoset polymer is selected from the group consisting of polystyrene, high-impact polystyrene, poly (acrylonitrile butadiene styrene), polycarbonates, PC-ABS blends, polyolefins, polyesters, polyamides, and epoxy resins.

12. The polymer composition of claim 11 wherein the thermoplastic or thermoset polymer is a thermoplastic polymer selected from the group consisting of polystyrene and high-impact polystyrene.

13. The polymer composition of claim 1 wherein the thermoplastic or thermoset polymer is selected from the group consisting of polystyrene, high-impact polystyrene, poly (acrylonitrile butadiene styrene), polycarbonates, PC-ABS blends, polyolefins, polyesters, polyamides, and epoxy resins.

14. The polymer composition of claim 13 wherein the thermoplastic or thermoset polymer is a thermoplastic polymer selected from the group consisting of polystyrene and high-impact polystyrene.

15. A halogenated non-polymeric phenyl ether flame retardant comprising halogenated non-polymeric phenyl ethers of general formula (I):

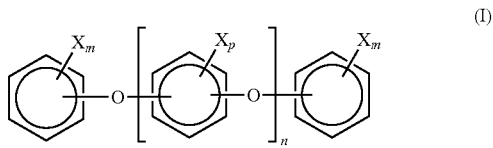

(I)

wherein each X is independently Cl or Br, n is an integer of 0, 1, 2, 3, 4, 5, or 6 or more, each m is independently an integer of 1 to 5 and each p is independently an integer of 1 to 4, wherein the flame retardant comprises, based on the total weight of halogenated non-polymeric phenyl ethers of formula (I):

from about 30 to about 50% 3-ring halogenated phenyl ethers, from about 30 to about 60% 4-ring halogenated phenyl ethers, from about 1 to about 15% 5-ring halogenated phenyl ethers, and less than 15% total of halogenated phenyl ethers containing 2-, 6-, 7-, 8- or a higher number of phenyl rings, provided that, when each X is Cl, the total amount halogen in the flame retardant is from about 50 wt % to about 65 wt % and when each X is Br, the total amount of halogen in the flame retardant is from about 70 wt % to about 79 wt %, and wherein from about 30% to about 80% of the halogenated non-polymeric phenyl ethers of formula (I) present in the composition are fully halogenated, and from about 70% to about 20% of all halogenated non-polymeric phenyl ethers are partially halogenated.

16. The flame retardant of claim 15, wherein from about 35% to about 75% of all halogenated non-polymeric phenyl ethers are fully halogenated and from about 65% to about 25% of all halogenated non-polymeric phenyl ethers are partially halogenated.

17. The flame retardant of claim 15 comprising, based on the total weight of the flame retardant, from about 30 to about 45% of 3-ring halogenated phenyl ethers, from about 35 to about 60% of 4-ring halogenated phenyl ethers, from about 1 to about 10% of 5-ring halogenated phenyl ethers, from about 1 to about 10% of 6-ring halogenated phenyl ethers, from about 0.1 to about 4% of 7-ring halogenated phenyl ethers, from about 0 to about 2% of 8-ring halogenated phenyl ethers, and 0 to about 1% of 2-ring halogenated di-phenyl ethers.

18. The flame retardant of claim 15, wherein each X is bromine.

19. The flame retardant of claim 8, wherein each X is bromine.

* * * * *